United States Patent
Zhang et al.

(10) Patent No.: US 10,932,805 B2
(45) Date of Patent: Mar. 2, 2021

(54) MEDICAL FORCEPS

(71) Applicant: ANREI MEDICAL (HANGZHOU) CO., LTD., Zhejiang (CN)

(72) Inventors: Rongnan Zhang, Zhejiang (CN); Liming Wang, Zhejiang (CN); Da Lei, Zhejiang (CN)

(73) Assignee: ANREI MEDICAL (HANGZHOU) CO., LTD., Zhejiang (CN)

( * ) Notice: Subject to any disclaimer, the term of this patent is extended or adjusted under 35 U.S.C. 154(b) by 0 days.

(21) Appl. No.: 16/631,168

(22) PCT Filed: May 10, 2019

(86) PCT No.: PCT/CN2019/086386
§ 371 (c)(1),
(2) Date: Jan. 15, 2020

(87) PCT Pub. No.: WO2019/223554
PCT Pub. Date: Nov. 28, 2019

(65) Prior Publication Data
US 2020/0222073 A1  Jul. 16, 2020

(30) Foreign Application Priority Data
May 25, 2018 (CN) .......................... 201810517098.6

(51) Int. Cl.
*A61B 17/29* (2006.01)
*A61B 10/04* (2006.01)
(Continued)

(52) U.S. Cl.
CPC .............. *A61B 17/29* (2013.01); *A61B 10/04* (2013.01); *A61B 10/06* (2013.01);
(Continued)

(58) Field of Classification Search
CPC ............ A61B 17/29; A61B 2017/2902; A61B 2017/2903; A61B 2017/2912;
(Continued)

(56) References Cited

U.S. PATENT DOCUMENTS 5,695,521 A * 12/1997 Anderhub .............. A61B 17/29
606/205
5,810,876 A * 9/1998 Kelleher ................ A61B 10/06
606/170
(Continued)

FOREIGN PATENT DOCUMENTS

CN   201101542   8/2008
CN   201143210   11/2008
(Continued)

OTHER PUBLICATIONS

"International Search Report (Form PCT/ISA/210) of PCT/CN2019/086386", dated Jul. 31, 2019, with English translation thereof, pp. 1-5.

*Primary Examiner* — Diane D Yabut
(74) *Attorney, Agent, or Firm* — JCIPRNET

(57) ABSTRACT

A medical forceps includes a handle, a traction string, a sleeve tube, a forceps base, a push-pull rod, two connecting members and two forceps jaws. The sleeve tube is connected to the forceps base. The traction string passes through the flexible spring tube and the forceps base, one end of the traction string is connected to the handle, and the other end thereof is connected to the push-pull rod. Middle parts of the two forceps jaws are hinged by a hinge shaft mounted on the forceps base. A lower part of the forceps jaw is hinged to one end of the respective connecting member, and the other end of the connecting member is hinged to the push-pull rod. The push-pull rod has two hinge centers for being respectively hinged to the two connecting members arranged in a crossed manner. The push-pull rod has two hinge centers.

6 Claims, 3 Drawing Sheets

(51) Int. Cl.
*A61B 10/06* (2006.01)
*A61B 17/00* (2006.01)

(52) U.S. Cl.
CPC ........... *A61B 2017/00477* (2013.01); *A61B 2017/2902* (2013.01); *A61B 2017/2912* (2013.01); *A61B 2017/2947* (2013.01)

(58) Field of Classification Search
CPC .... A61B 2017/2919; A61B 2017/2932; A61B 2017/2939; A61B 2017/2947; A61B 10/04; A61B 10/06
See application file for complete search history.

(56) References Cited

U.S. PATENT DOCUMENTS

| | | | |
|---|---|---|---|
| 2004/0127890 | A1 | 7/2004 | Bacher |
| 2006/0258954 | A1* | 11/2006 | Timberlake ............ A61B 10/06 600/564 |
| 2013/0131544 | A1* | 5/2013 | Bowden ................ A61B 10/06 600/564 |

FOREIGN PATENT DOCUMENTS

| | | |
|---|---|---|
| CN | 101530340 | 9/2009 |
| CN | 103142258 | 6/2013 |
| CN | 204033383 | 12/2014 |
| CN | 108969026 | 12/2018 |

* cited by examiner

MEDICAL FORCEPS

CROSS-REFERENCE TO RELATED APPLICATION

This application is a 371 of international application of PCT application serial no. PCT/CN2019/086386, filed on May 10, 2019, which claims the priority benefit of China application no. 201810517098.6, filed on May 25, 2018. The entirety of each of the above mentioned patent applications is hereby incorporated by reference herein and made a part of this specification.

BACKGROUND

Technical Field

The present disclosure relates to a medical instrument, in particular to a medical forceps used under an endoscope.

Description of Related Art

With the rapid development of endoscopes and other related technologies, as cancer diseases are frequently diagnosed nowadays, using biopsy forceps to sample biopsies and perform biopsy and pathological analysis under endoscopes is of high significance.

At present, with regard to the biopsy forceps in the field of endoscopic biopsy sampling, no matter whether the biopsy forceps has the four-bar or wire hook structure or other similar structures, they tend to have insufficient occlusal force. As a result, when the tissue is clamped by the forceps, the tissue tends to be torn and bleed when the forceps cup is closed, and subsequent hemostasis treatment is required. Accordingly, the operation time and treatment costs are increased and more pain is brought to patients.

With regard to the known structure, the handle is pushed, and the pushing force is transmitted to the push-pull rod of the forceps head assembly through a traction string, thereby driving the forceps cup to open and close. The main structure of the known forceps head assembly is: a forceps cup, a cup holder, a connecting piece and a push-pull rod. The push-pull rod is of a single hole structure, and the connecting piece is connected to left and right one of the push-pull rod hole.

For the known structure, during the opening and closing process of the forceps cup, since the push-pull rod is a single-hole push-pull rod with only one hinge center, the forceps cup is close to the "dead point" position of the four-bar mechanism when the forceps cup is engaged, and the transmission angle is smaller, which affects the smoothness of pushing and also greatly reduces the occlusal force transmitted from the handle to the forceps cup, and consequently directly affects the performance of the biopsy forceps.

SUMMARY

Technical Problem

In order to solve the above technical problems, the purpose of the present disclosure is to provide a medical forceps with strong occlusal force and more flexible use.

Solution to Problem

Technical Solution

In order to achieve the above purpose, the present disclosure adopts the following technical solutions.

A medical forceps includes a handle, a traction string, a sleeve tube, a forceps base, a push-pull rod, two connecting members and two forceps jaws. The sleeve tube is connected to the forceps base. The traction string passes through the sleeve tube and is configured in the forceps base, one end of the traction string is connected to the handle, and the other end thereof is connected to the push-pull rod. Middle parts of the two forceps jaws are hinged by means of a hinge shaft, and the hinge shaft is mounted on the forceps base. A lower part of the forceps jaw is hinged to one end of each of the connecting members, and the other end of each of the connecting members is hinged to the push-pull rod. The push-pull rod has two hinge centers for being respectively hinged to the two connecting members, and the two connecting members are arranged in a crossed manner.

Preferably, a connection line between the two hinge centers on the push-pull rod is (c), and a length of (c) ranges from 0.2 mm to 3 mm. In this way, it is possible to further ensure that the forceps has the maximum occlusal force and ensures flexible pushing.

Preferably, a connection line between two hinge centers on the same forceps jaw is (a), and a connection line between two hinge centers on the same connecting member is (b). On one forceps jaw and one of the connecting members hinged to each other, an angle between (a) and (b) is a; on one of the connecting members and the push-pull rod hinged to each other, an angle between (b) and (c) is β. When the two forceps jaws are engaged, β ranges from 40° to 80°, α ranges from 90° to 180°. In this manner, it is possible to further ensure that the forceps has the maximum occlusal force and ensures flexible pushing.

Preferably, a length of (a) ranges from 0.5 mm to 20 mm, and a length of (b) ranges from 0.5 mm to 20 mm. When two forceps claws are open, α ranges from 1° to 180°, β ranges from 1° to 90°. The length of (a) of the two forceps jaws can be the same or different, the length of (b) of each of the two connecting members can be the same or different, and (c) can be perpendicular to a moving direction of the push-pull rod or can have a certain angle. When the forceps needs to be centered for engagement, the length of (a) of the two forceps jaws is the same, the length of (b) of each of the two connecting members is also the same, and (c) is perpendicular to the moving direction of the push-pull rod.

Preferably, an upper part of the push-pull rod is provided with two second hinge holes at intervals, and the connecting members are respectively hinged with the push-pull rod through the second hinge holes.

Preferably, the upper part of the push-pull rod is provided with a hinge joint, and two second hinge holes are respectively provided at the left and right ends of the hinge joint.

Preferably, the forceps jaw is a forceps cup, and the forceps cup includes a cup mouth, a short hinge piece, and a long hinge piece. The short hinge piece is formed by extending downward from a front side of a lower part of the cup mouth, and the long hinge piece is formed by extending downward from a rear side of the lower part of the cup mouth, and a gap is provided between the short hinge piece and the long hinge piece.

As a preferred solution: both ends of a lateral side of each of the connecting members are provided with hinge bars, the two ends of each of the connecting members form a circular arc corner, and a radius of the circular arc corners of the two ends of the connecting member are different, and the two connecting members are respectively arranged on the front and rear sides of the push-pull rods.

As a preferred solution: front and back sides of the forceps base are extended upward to form two support pieces, and each of the support pieces is provided with a first hinge hole for setting a shaft.

As a preferred solution: the forming process of the connecting piece is machining, etching, stamping or powder metallurgy, the forming process of the push-pull rod may be machining, stamping or powder metallurgy, and the forming process of the forceps base is machining, stamping or powder metallurgy.

Advantageous Effect of Disclosure

Advantageous Effect

The push-pull rod of the present disclosure adopts a double hinge center structure, so that the forceps jaw, the connecting member and the push-pull rod form a staggered five-bar mechanism, which avoids the problem that the four-bar mechanism is close to the "dead point" during the engagement in the related art, and increases the transmission angle, thereby ensuring that the forceps can be pushed flexibly, and the occlusal force of the forceps is enhanced, so that the efficiency and accuracy of the biopsy forceps for taking the tissue can be improved.

DESCRIPTION OF THE MOST PREFERABLE EMBODIMENTS

Most Preferable Embodiment of Present Disclosure

Figure 1:
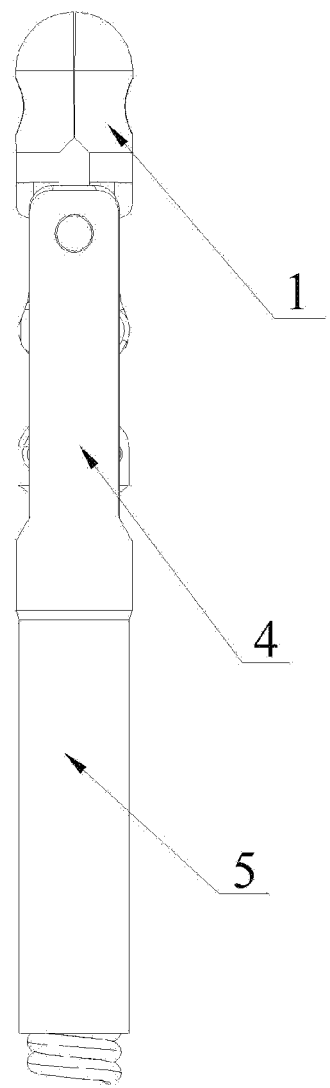
FIG. 1 is a schematic structural view of a closed state of a forceps of an embodiment 1.
Figure 2:
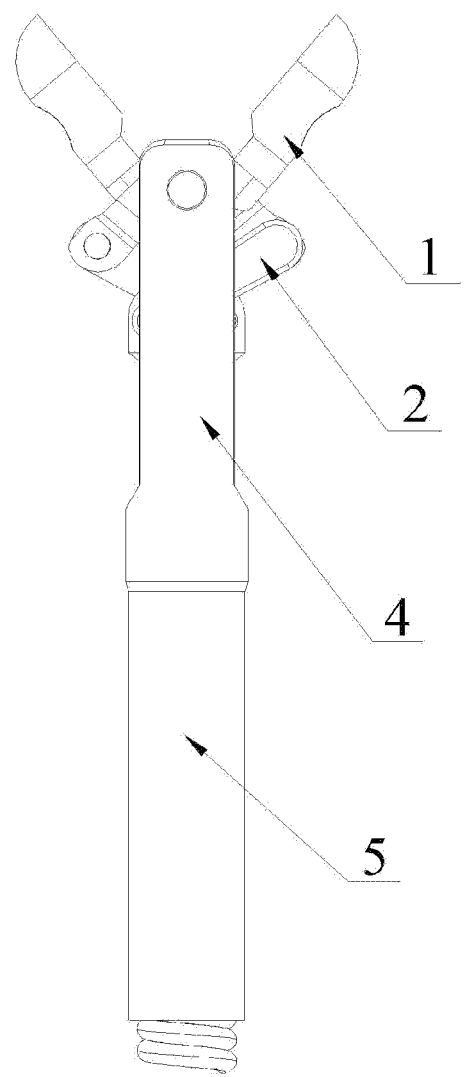
FIG. 2 is a schematic structural view of an open state of the forceps of the embodiment 1.

The embodiments of the present disclosure are described in detail below. Examples of the embodiments are shown in the drawings, wherein the same or similar reference numerals indicate the same or similar elements or elements having the same or similar functions. The embodiments described below with reference to the drawings are exemplary and are intended to explain the present disclosure, and should not be construed as limiting the present disclosure.

A medical forceps as shown in FIG. 1 to FIG. 8 includes a handle, a traction string, a sleeve tube 5, a forceps base 4, a push-pull rod 3, two connecting members 2 and two forceps jaws 1. The sleeve tube 5 is connected to the forceps base 4. The traction string passes through the sleeve tube 5 and is configured in the forceps base 4. One end of the traction string is connected to the handle, and the other end of the traction string is connected to the push-pull rod 3. Middle parts of the two forceps jaws 1 are hinged by means of a hinge shaft, and the hinge shaft is mounted on the forceps base 4. A lower part of each of the forceps jaws 1 is hinged to one end of each of the connecting members 2, and the other end of each of the connecting members 2 is hinged to the push-pull rod 3. The push-pull rod 3 has two hinge centers for being respectively hinged to the two connecting members 2; and the two connecting members 2 are arranged in a crossed manner.

Figure 3:
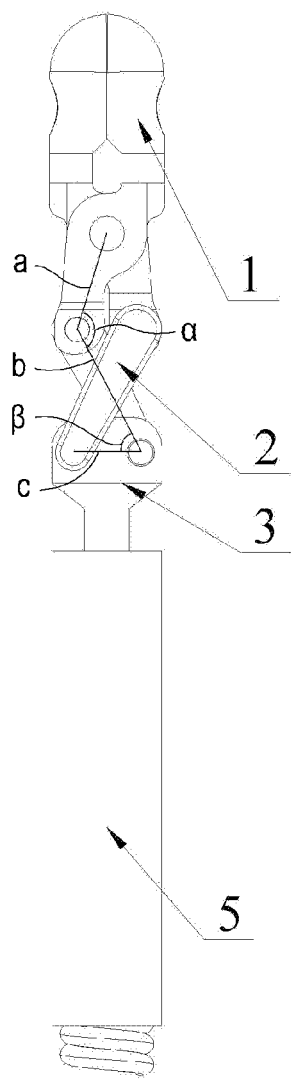
FIG. 3 is a schematic structural view of the closed state of the forceps without a forceps base of the embodiment 1.

Preferably, a connection line between the two hinge centers on the push-pull rod 3 is (c), and a length of (c) ranges from 0.2 mm to 3 mm so as to ensure that the forceps has the maximum occlusal force and ensures flexible pushing. In the embodiment, a connection line between two hinge centers on the same forceps jaw 1 is (a), and a connection line between two hinge centers on the same connecting member 2 is (b). A connection line between the two hinge centers on the push-pull rod 3 is (c). On one of the forceps jaws 1 and one of the connecting members 2 hinged to each other, an angle between (a) and (b) is α; on one of the connecting members 2 and the push-pull rod 3 hinged to each other, an angle between (b) and (c) is β. As shown in FIG. 3, when the two forceps jaws 1 are engaged, β ranges from 40° to 80°, α ranges from 90° to 180°. In this manner, it is possible to further ensure that the forceps has the maximum occlusal force and ensures flexible pushing. In the embodiment, the length of (a) ranges from 0.5 mm to 20 mm, and a length of (b) ranges from 0.5 mm to 20 mm. When two forceps claws 1 are open, a is 1° to 180°, β is 1° to 90°. The length of (a) of the two forceps jaws can be the same or different, the length of (b) of the two connecting members can be the same or different, and (c) can be perpendicular to a moving direction of the push-pull rod or can have a certain angle. In the embodiment, when the forceps needs to be centered for engagement, the length of (a) of the two forceps jaws is the same, the length of (b) of the two connecting members is also the same, and (c) is perpendicular to the moving direction of the push-pull rod.

Figure 7:
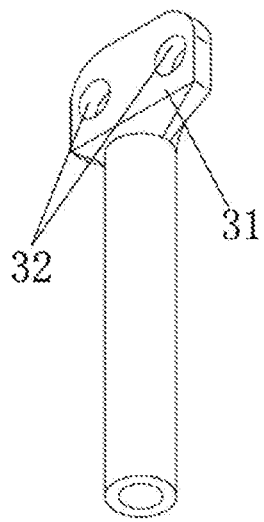
FIG. 7 is a schematic structural view of a push-pull rod of the embodiment 1.

In the embodiment, the upper part of the push-pull rod 3 is provided with two second hinge holes 32 at intervals, and another ends of the two connecting members 2 are respectively hinged in the two second hinge holes 32, and the two connecting members 2 are arranged in a crossed manner. As shown in FIG. 7, an upper part of the push-pull rod 3 is provided with a hinge joint 31, and two second hinge holes 32 are respectively provided at left and right ends of the hinge joint 31. In other embodiments, the hinge shaft of the connecting members and the push-pull rod may be securely connected or integrally formed on the push-pull rod.

Figure 4:
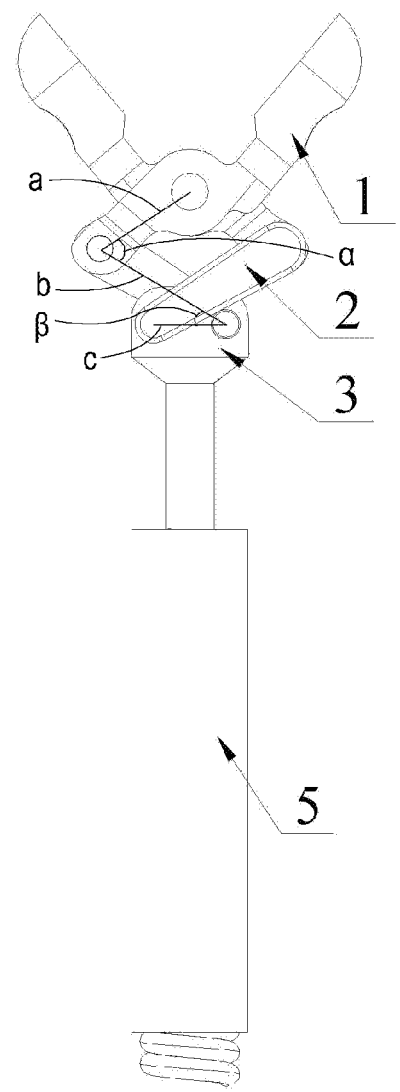
FIG. 4 is a schematic structural view of the closed open state of the forceps without the forceps base in the embodiment 1.

The structure of the present disclosure makes the traction string to drive the push-pull rod to move through the handle which pushes forward and backward. The connecting members serve the function of connecting the push-pull rod and the forceps jaw to transmit the pushing of the push-pull rod to open or close the forceps jaws. As shown in FIG. 3 and FIG. 4, the other end of the connecting member 2 on the left side of the present disclosure is hinged in the second hinge hole 32 on the right side, and the other end of the connecting member 2 on the right side is hinged in the second hinge hole 32 on the left side. As compared with the single hinge center structure, since the minimum included angle formed by the two connecting members becomes larger, the component force transmitted to open or close the forceps jaw by the push-pull rod is also increased, thereby improving the occlusal force and opening force of the forceps jaws so that the pushing is smoother and the use of the forceps is more flexible.

The two ends of the push-pull rod 3 are connected to the connecting member and the traction string respectively. The double hinge center structure is adopted, and a hole distance and a hole diameter are not limited. The optimal selection is determined based on the size of the entire structure. Compared with the single hinge center structure, the advantages of the double hinge center structure are that it has a more reasonable layout and can sufficiently serve the function of the transmission component, thereby avoiding "dead point" and increasing the transmission angle, such that the flexibility of handle pushing can be improved while the pushing-pulling force of the handle can be converted into the occlusal force and opening force of the forceps jaw at the maximum level. The forming process of the push-pull rod can be machining, stamping or powder metallurgy, but it is not limited to these three forming processes.

Figure 5:
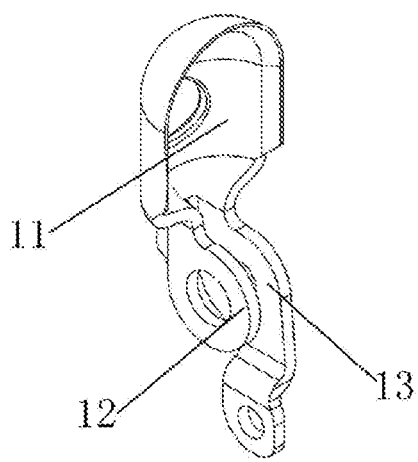
FIG. 5 is a schematic structural view of a forceps cup of the embodiment 1.

In this embodiment a biopsy forceps is exemplified, the forceps base 4 is a cup holder, the sleeve tube 5 is a flexible spring tube, each of the connecting members 2 is a connecting piece, and each of the forceps jaws 1 is a forceps cup. In other embodiments, it can also be a foreign body forceps or other medical instrument. As shown in FIG. 5, the forceps cup includes a cup mouth 11, a short hinge piece 12 and a long hinge piece 13. The short hinge piece is formed by extending downward from a front side of a lower part of the cup mouth 11, the long hinge piece 13 is formed by extending downward from a rear side of the lower part of the cup mouth 11, and a gap is provided between the short hinge piece 12 and the long hinge piece 13.

The forceps cup of this embodiment takes the tissue by opening and closing the cup mouth. The depth of the cup mouth determines the capacity of the taken tissue. The structure of the forceps cup can adopt a smooth structure as shown in FIG. 5 or may include a teeth structure, the present disclosure is not limited to the above two structure. The forming process of the forceps cup can be stamping, powder metallurgy, machining, but not limited to these three forming processes.

Figure 6:
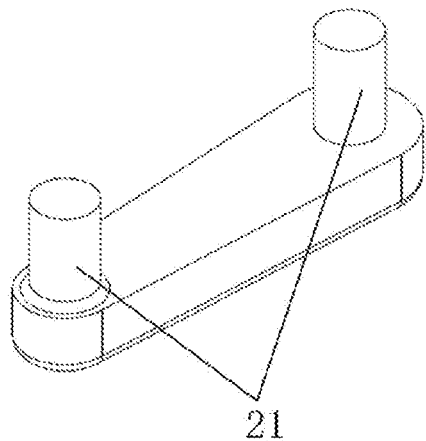
FIG. 6 is a schematic structural view of a connecting member of the embodiment 1.

As shown in FIG. 6, both ends of a lateral side of each of the connecting members 2 are provided with a hinge bar 21, the two ends of each of the connecting members 2 form a circular arc corner, and a radius of the circular arc corners of the two ends of the connecting member 2 are different, and the two connecting members 2 are respectively arranged on the front and rear sides of the push-pull rods 3. The connecting members 2 are connected to the push-pull rod and the forceps cup to serve the function of transmitting movement. The forming process of the connecting member is machining, etching, stamping and powder metallurgy, but not limited thereto.

Figure 8:
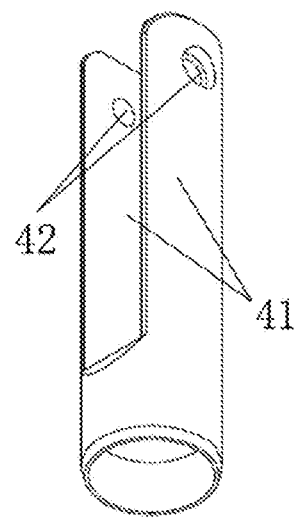
FIG. 8 is a schematic structural view of the forceps base of the embodiment 1.

As shown in FIG. 8, front and back sides of the forceps base 4 are extended upward to form two support pieces 41, and each of the support pieces 41 is provided with a first hinge hole 42 for setting a shaft. A lower end of the forceps base 4 and the sleeve tube are connected to serve the function of fixing and supporting the opening and closing of the entire forceps cup assembly, thereby preventing skewing and loosening and avoiding that the force level and accuracy of taking the issue is affected. The forming process of the forceps base includes but is not limited to machining, stamping and powder metallurgy.

In this embodiment, the sleeve tube 5 is a flexible spring tube (coated or uncoated). The sleeve tube is connected to the forceps base, thereby supporting and fixing the forceps cup so that the forceps cup does not incline. Meanwhile, when the forceps cup takes the tissue, a strong occlusal force is required, and the sleeve tube and forceps base serve to provide the strong supporting force, thereby avoiding deformation when the tissue is taken and preventing the effect and efficiency of taking the tissue from being affected.

Embodiment of the Present Disclosure

The present disclosure aims to design a biopsy forceps with double hole push-pull rod so as to solve the existing problem that when the biopsy forceps takes the tissue, the occlusal force is insufficient and as a result the issue cannot be successfully taken or the tissue is torn and bleed and so on. With the characteristic of the double hinge center structure of the push-pull rod, it is possible to effectively avoid the problem in the existing art that the pulling force of the push-pull rod is close to the "dead point" during the transmission process, and the smoothness of pushing can be enhanced while the occlusal force of taking the tissue can be strengthened, such that the biopsy tissue-related operation can be accurately and rapidly completed, and the safety and efficiency of the operation can be significantly improved.

According to the operation principle and method of the present disclosure, not only that the structure of the double-hole push-pull rod is sought to be protected, but the forming process of each related component is also within the scope of the present disclosure, and the medical forceps of the present disclosure include but is not limited to biopsy forceps and foreign body forceps.

In other embodiments, the present disclosure may also have many variations. For example, in the above embodiment, the two hinged holes of the double-hole push-pull rod are designed into one hole.

It should be noted that the above embodiments are only representative examples of the present disclosure. Any simple modifications, equivalent changes and amendments made to the above embodiments in accordance with the nature of the present disclosure shall be regarded as falling within the scope of the present disclosure.

What is claimed is:

1. A medical forceps comprising a handle, a traction string, a sleeve tube, a forceps base, a push-pull rod, two connecting members and two forceps jaws, wherein the sleeve tube is connected with the forceps base, the traction string passes through the sleeve tube and is configured in the forceps base, one end of the traction string is connected with the handle, and the other end of the traction string is connected with the push-pull rod, a middle part of each of the two forceps jaws is hinged by a hinge shaft and the hinge shaft is mounted on the forceps base, a lower part of each of the forceps jaws is hinged with one end of each of the connecting members, and the other end of each of the connecting members is hinged with the push-pull rod, the push-pull rod has two hinge centers for respectively hinging with the two connecting members, and the two connecting members are arranged in a crossed manner; wherein an upper part of the push-pull rod is provided with a hinge joint, and the two hinge centers are respectively disposed at left and right ends of the hinge joint, the hinge joint is hinged to the two connecting members respectively through the two hinge centers;

wherein one of the two hinge centers is disposed at the left end of the hinge joint along a first axis, and the other one of the two hinge centers is disposed at the right end of the hinge joint along a second axis, wherein the first axis is different from the second axis;

wherein a connection line between the two hinge centers on the push-pull rod is (c), and a length of (c) ranges from 0.2 mm to 3 mm;

wherein a connection line between two hinge centers on the same forceps jaw is (a), and a connection line between two hinge centers on the same connecting member is (b); on one of the forceps jaws and one of the connecting members hinged to each other, an angle between (a) and (b) is α; on one of the connecting members and the push-pull rod hinged to each other, an angle between (b) and (c) is β; when the two forceps jaws are engaged, β ranges from 40° to 80°, α ranges from 90° to 180°;

wherein a length of (a) ranges from 0.5 mm to 20 mm, and a length of (b) ranges from 0.5 mm to 20 mm.

2. The medical forceps according to claim 1, wherein front and rear sides of the forceps base extend upward to form two support pieces, and each of the support pieces is provided with a first hinge hole for configuring the hinge shaft.

3. The medical forceps according to claim 2, wherein the two hinge centers are two second hinge holes respectively provided at the left and right ends of the hinge joint, and the connecting members are respectively hinged with the push-pull rod through the second hinge holes.

4. The medical forceps according to claim 1, wherein each of the forceps jaws is a forceps cup, the forceps cup comprises a cup mouth, a short hinge piece and a long hinge piece, the short hinge piece is formed by extending downward from a front side of a lower part of the cup mouth, the long hinge piece is formed by extending downward from a rear side of the lower part of the cup mouth, and a gap is provided between the short hinge piece and the long hinge piece.

5. The medical forceps according to claim 1, wherein both ends of a lateral side of each of the connecting members are provided with hinge bars, the two ends of each of the connecting members form a circular arc corner, a radius of the circular arc corners of the two ends of each of the connecting members are different, and the two connecting members are respectively arranged on front and rear sides of the push-pull rods.

6. The medical forceps according to claim 1, wherein a forming process of the connecting member is machining, etching, stamping or powder metallurgy, a forming process of the push-pull rod is machining, stamping or powder metallurgy, and a forming process of the forceps base is machining, stamping or powder metallurgy.

* * * * *